United States Patent [19]

Cawood, Jr. et al.

[11] 4,043,328
[45] Aug. 23, 1977

[54] UROLOGICAL DRAPE

[75] Inventors: Charles D. Cawood, Jr., Houston, Tex.; John S. Ziegler, Arlington Heights, Ill.

[73] Assignee: American Hospital Supply Corporation, Evanston, Ill.

[21] Appl. No.: 691,596

[22] Filed: June 1, 1976

[51] Int. Cl.² ............................................. A61B 19/06
[52] U.S. Cl. ................................................. 128/132 D
[58] Field of Search ............... 128/132 D, 132 R, 292, 128/157

[56] References Cited

U.S. PATENT DOCUMENTS

| 1,491,011 | 4/1924 | Hodgin | 128/132 D |
| 3,397,692 | 8/1968 | Creager et al. | 128/132 D |
| 3,923,052 | 12/1975 | Zoephel | 128/132 D |

Primary Examiner—Lawrence W. Trapp
Attorney, Agent, or Firm—Tilton, Fallon, Lungmus, Chestnut & Hill

[57] ABSTRACT

A disposable unitary drape particularly suited for use in performing transurethral surgery of the bladder and prostate, and similar operations. A thin flexible finger cot projects from the body of the drape, the cot having a bulbous distal end portion and an elongated neck portion of reversed taper and reduced wall thickness. An annular retention rib projects outwardly from the cot at the juncture of the neck and end portions and, in one embodiment, the wall thickness of the neck portion is even further reduced in an arcuate intermediate section to increase tactile sensitivity in that zone for the surgeon. The cot may be supplied in longitudinally collapsed form. Because of its configuration and construction, the cot tends to be self-retaining in use.

23 Claims, 5 Drawing Figures

UROLOGICAL DRAPE

BACKGROUND

In transurethral surgery, where a resectoscope is inserted through the urethra to remove that portion of the prostate gland (adenoma) which obstructs the urinary passage, the surgeon ordinarily uses a finger of his other hand to palpate and adjust the position of the prostate during cutting by pressing upwardly against the wall of the rectum. To avoid contamination of the gloved hand and surgical field generally, a drape is commonly used that is equipped with a sheath or cot intended to be inserted into the rectum and to remain in place throughout the operative procedure.

Although efforts have been made to develop urological drapes with cots which are self-retaining in use, such efforts have been generally unsuccessful. Thus, cots have been devised with external annular ribs in close proximity to the body portions of the drapes, presumably in the expectation that such a rib will engage and be retained by the anal sphincter. In practice, however, such retention has been found undependable. Problems may arise, for example, should the surgeon find it necessary to withdraw his finger from the cot and thereafter reinsert it — an action which may normally occur many times during such an operation. With each withdrawal, there is a risk that the cot will also be extracted or expelled. Furthermore, should the surgeon's gloved finger stick to the inside surface of the natural or synthetic rubber cot, evagination of the cot is likely to occur as the finger is extracted, the cot there being everted and pulled from the patient, creating risks of contamination and otherwise complicating the operative procedure.

Transurethral prostatic resection is discussed in detail in texts such as R. M. Nesbit et al., *Transurethral Prostatic Resection,* Nelson's Loose-Leaf Surgery, 305–320 (1949, Thomas Nelson & Sons). Typical urological drapes are depicted and described in V. Mueller Catalog, 369 (1968). Other references illustrating the state of the prior art are U.S. Pat. Nos. 1,491,011, 2,123,343, and 2,406,600.

SUMMARY

This invention is concerned with an improved disposable unitary urological drape having a finger cot or sheath which is self-retentive in use and which provides a high level of tactile sensitivity for the surgeon who uses the cot in palpating the prostate through the rectum during adenomectomy. Specifically, the cot portion of the drape is virtually incapable of total evagination and, therefore, cannot be pulled inside-out and thereby extracted by any of the forces normally occurring during an operative procedure, particularly those forces which develop as the surgeon withdraws his gloved finger from the cot.

In brief, the drape consists of a sheet of flexible material having a generally centrally-disposed opening from which a finger cot projects. The cot, which may be formed integrally with the sheet or as a separate element permanently secured thereto, is formed of thin stretchable material such as natural or synthetic rubber. In configuration, the cot is reversely tapered, having an elongated neck portion which terminates in an enlarged closed free end portion. An outwardly-projecting annular rib is disposed near the distal end of the cot at the boundary of the neck and head portions. The enlarged end portion has a wall thickness substantially greater than that of the elongated reversely-tapered neck portion. In the best form presently known for practicing the invention, the neck portion, in addition to having a thickness less than the end portion, has an upper arcuate section of even further reduced thickness to provide a readily deformable zone for palpation of the prostate or base of the bladder during transurethral surgery.

While the thin flexible neck portion is capable of being folded upon itself into a collapsed condition, the greater diameter of the end or head portion necessarily results in retraction of the head to a position outside of, rather than within, the neck. Thus, should contact between a surgeon's gloved finger and the inside surface of the cot result in a stricking action, any effort to withdraw the finger from the cot will cause a peeling separation between the sticking surfaces.

Palpation of the prostate occurs through the application of force upwardly against the side wall of the cot's neck portion at a point or zone disposed inwardly (proximally) with respect to the annular rib and the closed end portion. While the rib performs a retentive function, aided by the stiffening action of the relatively thick head portion, such retentive engagement between the rib and the rectal wall tends to occur inwardly beyond the prostate or, in any event, at a substantial distance inwardly from the anal sphincter. In addition to providing a stiffening action for the rib, the increased thickness of the cot's head portion tends to reduce stretching and possible tearing of the cot at the point of force application during insertion.

Other advantages and objects of the invention will become apparent from the description and drawings.

DRAWINGS

DESCRIPTION

Figure 1:
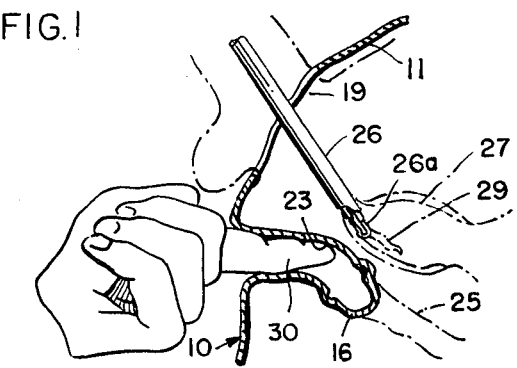
FIG. 1 is a longitudinal (sagittal) sectional view illustrating an operative procedure in which the drape of this invention is utilized.

Referring to the drawings, the numeral 10 generally designates a urological drape comprising a sheet 11 of flexible material having top, side, and bottom edges 12–14 and having a generally centrally-located opening 15 (FIG. 4) from which a finger cot or sheath 16 projects. The cot is formed of flexible stretchable material such as natural or synthetic rubber. It may be formed integrally with the sheet or, if desired, may be formed as a separate part and joined to the sheet about opening 15 by adhesive or by any other suitable means. This, if it is desired to utilize a typical fluid-resistant but gas-permeable reinforced paper in the fabrication of the sheet, the latter construction would be employed.

Figure 2:
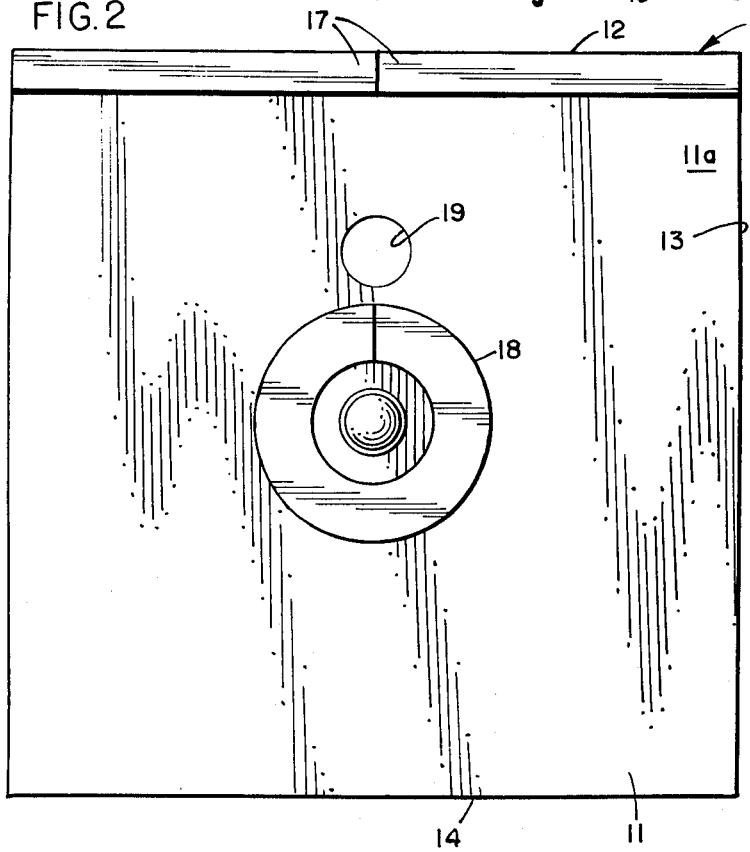
FIG. 2 is a plan view showing the front of the drape.
Figure 3:
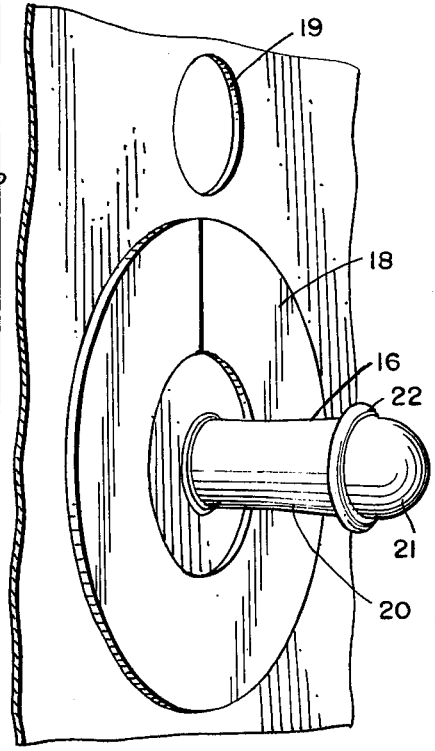
FIG. 3 is an enlarged fragmentary perspective view illustrating the drape in the vicinity of the cot portion thereof.

Suitable means may be provided for securing the front surface 11a of the sheet directly to the patient. In FIG. 2, protective strips 17 may be peeled away to expose areas of pressure sensitive adhesive carried along the upper edge portion of the sheet. Similarly, an annular cover 18 conceals a coating of pressure sensitive adhesive extending about the cot for adhesively securing the drape in the general area of the perineum.

Opening 19 is provided directly above the cot to receive the glans penis and scrotum, as schematically illustrated in FIG. 1.

Cot or sheath 16 is reversely tapered, having an elongated neck portion 20 and an enlarged head or closed end portion 21. As shown most clearly in FIG. 4, the neck portion gradually increases in size as it extends forwardly, that is, away from the body of the drape. An annular external rib or bead 22 extends about the cot at the boundary of the neck and head portions.

It will be noted that the thickness of the head portion 21 is substantially greater than the thickness of neck portion 20. Specifically, the wall thickness of the head portion should fall within the general range of 0.030 to 0.080 of an inch, whereas the thickness of the neck portion should fall within the general range of 0.010 to 0.050 of an inch. The result is that the head portion 21 is relatively stiff compared to the neck portion. As previously indicated, such stiffness, in addition to the larger size of the head relative to the neck, promotes retention of the inserted sheath because it resists collapse and reinforces the rib. Additionally, the reduced diameter of the neck, as compared to the head, permits the anal sphincter to grip the cot, thus further promoting the retention and resistance to eversion. Since the end wall of the head provides the focal point for the application of force during insertion of the sheath or cot, the greater thickness of that portion also reduces the danger of tearing and possible contamination.

Figure 4:
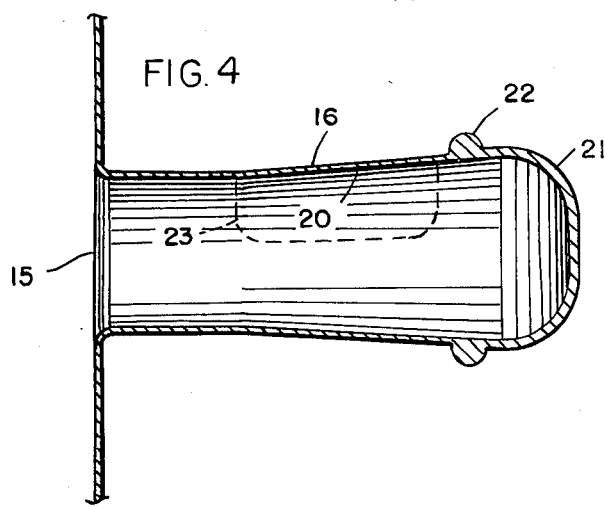
FIG. 4 is a longitudinal sectional view of the cot portion of the drape in extended condition.

In a preferred embodiment, the wall thickness of the neck portion 20 is reduced even further in an arcuate zone or section as represented in FIG. 4 by broken line 23. In general, section 23 extends longitudinally along a major portion of the length of the neck and has an angular dimension within the range of 90° to 180° degrees. The wall thickness in that section should not exceed 0.02 of an inch and should be as thin as is safe and practical to make it. Because of its reduced thickness, section 23 provides the surgeon with even greater tactile sensitivity when the prostate is palpated as illustrated in FIG. 1.

Figure 5:
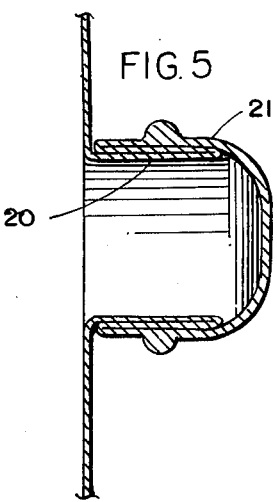
FIG. 5 is a sectional view similar to FIG. 4 but showing the cot in collapsed condition.

The drape may be marketed and stored with the sheath in a collapsed condition as illustrated in FIG. 5. It is to be noted that when the sheath or cot is so collapsed, neck portion 20 is folded upon itself and head portion 21 is not only disposed adjacent the main body of the drape but extends about the reversely-folded neck. A comparison of FIGS. 4 and 5 reveals that if a collapsing force were applied to the extended cot by reason of a retracting frictional force against the inside surface of section 23, the surfaces of frictional contact would necessarily separate from each other as the neck portion commenced its folding action. In other words, the fact that normal collapse of the cot occurs only with the head portion retracting into a position outside, not inside, of the neck, and with the distal portion of the neck folding rearwardly to the outside of the proximal portion, contributes significantly in achieving self-retention of the inserted and extended cot.

Since it is the zone of reduced thickness 23 that is directly contacted by the gloved finger of a surgeon during palpation of the prostate (FIG. 1) it is evident that the cot is of substantial length. The total length may range from approximately 3 to 5 inches, the preferred range being about 4 to 4.5 inches. As an example of an embodiment believed to constitute the best mode presently known for practicing the invention, the wall thickness of section 23 may be 0.015 of an inch, the thickness of the remainder of the neck portion may be 0.040 of an inch, the thickness of the head section may be 0.055 of an inch, the minimum inside neck diameter adjacent the body of the sheet should be at least 0.80 of an inch (the preferred dimension being 1.0), and the minimum inside diameter of the neck adjacent the rib should be at least 1.10 inches (the preferred dimension being 1.20).

In the operative procedure as shown in FIG. 1, cot 16 has been fully inserted into the rectum 25. Resectoscope 26 extends into the prostatic urethra 27. Cutting loop 26a of the resectoscope is depicted in somewhat schematic fashion in the process of slicing away a strip of prostate adenoma 29. The surgeon, with his finger 30 inserted into the cot and bearing upwardly against neck wall portion 23, palpates, supports, and adjusts the position of the prostate during the cutting operation.

While in the foregoing, embodiments of the inventions have been disclosed in considerable detail, it will be understood by those skilled in the art that many of those details may be varied without departing from the spirit and scope of the invention. We claim:

1. A urological drape for use in transurethral resections and similar operations, comprising a sheet of flexible material having a generally centrally-disposed opening therethrough, and a finger cot of flexible stretchable material extending from said sheet about said opening, said cot having an elongated neck portion and terminating in an enlarged closed free end portion, said neck portion gradually increasing in diameter towards said enlarged end portion.

2. The drape of claim 1 in which said enlarged end portion has a wall thickness substantially greater than that of said neck portion.

3. The drape of claim 2 in which said end portion has a wall thickness within the range of about 0.030 to 0.080 of an inch, and said neck portion has a wall thickness within the range of about 0.010 to 0.050 of an inch.

4. The drape of claim 3 in which said neck portion includes an arcuate section having a wall thickness substantially less than the remainder of said neck portion, said arcuate section providing a readily deformable zone for palpation of the prostate during transurethral resection.

5. The drape of claim 4 in which said arcuate section has a wall thickness no greater than 0.02 of an inch.

6. The drape of claim 5 in which said arcuate section extends longitudinally along a major portion of the length of said neck portion and has an angular dimension within the range of 90° to 180°.

7. The drape of claim 1 in which said neck portion is foldable upon itself into a collapsed condition wherein said enlarged head portion is retracted to a position adjacent said sheet and extends about said folded neck portion.

8. A urological drape for use in transurethral resections and similar operations, comprising a sheet of flexible material having a generally centrally-disposed opening therethrough, and a finger cot of flexible stretchable material extending from said sheet about said opening, said cot having an elongated neck portion and terminating in an enlarged closed free end portion, said neck portion gradually increasing in diameter towards said enlarged end portion, and an outwardly-projecting annular rib disposed at the boundary of said neck and head portions.

9. The drape of claim 8 in which said enlarged end portion has a wall thickness substantially greater than that of said neck portion.

10. The drape of claim 9 in which said end portion has a wall thickness within the range of about 0.030 to 0.080 of an inch, and said neck portion has a wall thickness within the range of about 0.010 to 0.050 of an inch.

11. The drape of claim 10 in which said neck portion includes an arcuate section having a wall thickness substantially less than the remainder of said neck portion, said arcuate section providing a readily deformable zone for palpation of the prostate during transurethral resection.

12. The drape of claim 11 in which said arcuate section has a wall thickness no greater than 0.02 of an inch.

13. The drape of claim 12 in which said arcuate section extends longitudinally along a major portion of the length of said neck portion and has an angular dimension within the range of 90° to 180°.

14. The drape of claim 8 in which said neck portion is foldable upon itself into a collapsed condition wherein said enlarged head portion is retracted to a position adjacent said sheet and extends about said folded neck portion.

15. A urological drape for use in transurethral resections and similar operations, comprising a sheet of flexible material having a generally centrally-disposed opening therethrough, and a finger cot of flexible stretchable material extending from said sheet about said opening, said cot having an elongated neck portion and terminating in an enlarged free end portion, said neck portion gradually increasing in diameter towards said enlarged end portion, said enlarged end portion having a wall thickness substantially greater than that of said neck portion, said cot having a total length within the range of about 3 to 5 inches.

16. The drape of claim 15 in which the neck portion of said cot has a minimum inside diameter adjacent said sheet of 0.80 of an inch.

17. The drape of claim 15 in which said neck portion has a minimum inside diameter adjacent said end portion of 1.10 inches.

18. The drape of claim 15 in which said end portion has a wall thickness within the range of about 0.030 to 0.080 of an inch, and said neck portion has a wall thickness within the range of about 0.010 to 0.050 of an inch.

19. The drape of claim 15 in which said neck portion includes an arcuate section having a wall thickness substantially less than the remainder of said neck portion, said arcuate section providing a readily deformable zone for palpation of the prostate during transurethral resection.

20. The drape of claim 19 in which said arcuate section has a wall thickness no greater than 0.02 of an inch.

21. The drape of claim 20 in which said arcuate section extends longitudinally along a major portion of the length of said neck portion and has an angular dimension within the range of 90° to 180°.

22. The drape of claim 15 in which said neck portion is foldable upon itself into a collapsed condition wherein said enlarged head portion is retracted to a position adjacent said sheet and extends about said folded neck portion.

23. The drape of claim 15 in which said cot has a total length within the range of about 4 to 5 inches.

* * * * *